United States Patent
Madabhushi et al.

(10) Patent No.: US 9,177,104 B2
(45) Date of Patent: Nov. 3, 2015

(54) DISCRIMINATIVELY WEIGHTED MULTI-SCALE LOCAL BINARY PATTERNS

(71) Applicant: Case Western Reserve University, Cleveland, OH (US)

(72) Inventors: Anant Madabhushi, Beachwood, OH (US); Haibo Wang, Binzhau (CN)

( * ) Notice: Subject to any disclaimer, the term of this patent is extended or adjusted under 35 U.S.C. 154(b) by 43 days.

(21) Appl. No.: 14/225,983

(22) Filed: Mar. 26, 2014

(65) Prior Publication Data

US 2014/0294272 A1 Oct. 2, 2014

Related U.S. Application Data

(60) Provisional application No. 61/806,578, filed on Mar. 29, 2013.

(51) Int. Cl.
*G06K 9/00* (2006.01)
*G06F 19/00* (2011.01)
*G06T 7/00* (2006.01)
*G01R 33/56* (2006.01)
*G06K 9/46* (2006.01)
*G06K 9/62* (2006.01)

(52) U.S. Cl.
CPC .......... *G06F 19/321* (2013.01); *G01R 33/5608* (2013.01); *G06F 19/3431* (2013.01); *G06K 9/0014* (2013.01); *G06K 9/00147* (2013.01); *G06K 9/4671* (2013.01); *G06K 9/6256* (2013.01); *G06T 7/0014* (2013.01); *G06T 7/0032* (2013.01); *G06T 7/0083* (2013.01); *G06T 7/0087* (2013.01); *G06T 2207/30081* (2013.01)

(58) Field of Classification Search
CPC ................ G06T 7/0014; G06T 7/0032; G06T 2207/30081; G06T 7/0083; G06T 7/0087; G01R 33/5608; G06K 9/4671; G06K 9/6256; G06K 9/0014; G06K 9/00147; G06F 19/321; G06F 19/3431
USPC .......................................... 382/131
See application file for complete search history.

(56) References Cited

U.S. PATENT DOCUMENTS

| 2012/0159656 A1* | 6/2012 | Gerber et al. ...................... 800/3 |
| 2015/0003741 A1* | 1/2015 | Zhang et al. ................... 382/199 |

* cited by examiner

*Primary Examiner* — Gregory F Cunningham

(57) ABSTRACT

Apparatus and methods associated with detecting prostate cancer (CaP) in a magnetic resonance (MR) image of a prostate of a CaP patient are described. One example apparatus includes logics that acquire an image of a prostate, learn a weighted vector, detect salient features in the image of the prostate, and generate a heatmap that facilitates detecting CaP. An image acquisition logic acquires a T2 weighted MR image of a prostate. A learning logic learns a weighted vector based on a set of positive LBP descriptors and a set of negative LBP descriptors extracted from the image at multiple scales. A salient feature detection logic detects salient features in the image based on the weighted vector and a pixel-by-pixel weighted Hamming matching of the image. A prediction logic generates a statistical probability heatmap based on the weighted vector and the weighted Hamming matching of the image.

20 Claims, 6 Drawing Sheets

DISCRIMINATIVELY WEIGHTED MULTI-SCALE LOCAL BINARY PATTERNS

CROSS REFERENCE TO RELATED APPLICATIONS

This application claims the benefit of U.S. Provisional Application No. 61/806,578 filed on Mar. 29, 2013.

BACKGROUND

Pixelwise template matching may be used to perform exhaustive searching of an entire image to find pixels similar to a query pixel. In patients undergoing treatment for prostate cancer (CaP) it is useful to distinguish cancerous tissue regions from benign tissue regions in magnetic resonance (MR) images on a pixel-by-pixel basis. A challenge to overcome when matching a pair of pixels is a trade-off between matching speed and accuracy. For example, a higher matching speed may be achieved at the cost of lower accuracy. Local Binary Pattern (LBP) pixelwise template matching is one conventional method of matching a local pixel feature to another pixel. Timo Ojala et al., *Multiresolution gray-scale and rotation invariant texture classification with local binary patterns*, IEEE TPAMI, vol. 24, pp. 971-987, 2002. The LBP descriptor of a pixel is a collection (e.g., string) of binary bits obtained by comparing the gray value of the pixel with the gray value of other pixels sampled within a ring of a certain radius centered on the pixel. The Hamming distance of LBP refers to the number of bits that are different. Computing the Hamming distance involves carrying out bitwise XOR operations that a computer may compute relatively quickly. Finding a distinctive ring radius facilitates extracting salient LBP descriptions.

Conventional LBP methods detect local Laplacian extrema. Lowe, *Distinctive image features from scale-invariant keypoints*, IJCV, vol. 60, pp. 91-110, 2004. Bay et al., *Speeded-up robust features (surf)*, CVIU, vol. 110, pp. 346-359, 2008. However, conventional methods are computationally costly, which substantially negates the benefits of LBP matching. In conventional methods, multiple radii may be sampled to guarantee measuring textual content a salient scale. By assuming independent sampling, measuring multi-scale LBP (MsLBP) is defined as the sum of the Hamming scores across individual scales. While conventional MsLBP is an improvement over basic LBP matching, conventional MsLBP under-emphasizes salient patterns while over-emphasizing insignificant patterns. In conventional MsLBP, a weight vector must be defined to account for the statistical significance of information at the salient scale by measuring the dissimilarity between a pair of multi-scale LBPs.

Learned binary projections facilitate indexing large image collections based on content. Strecha et al., *Ldahash: Improved matching with smaller descriptors*, IEEE TPAMI, vol. 34, pp. 66-78, 2012. However, conventional unsupervised hashing leads to binary codes that may offer no improvement over random binarization. Pauleve et al., *Locality sensitive hashing: A comparison of hash function types and querying mechanisms*, PRL, vol. 31, pp. 1348-1358, 2010. Weiss et al., *Spectral hashing*, in NIPS, 2008, pp. 1753-1760. With supervised learning imposed, supervised hashing explicitly learns a mapping that maximizes the distances among different classes. However, conventional supervised hashing suffers from a non-differentiable sign function. The non-differentiable sign function forces a relaxation of the objective function, which results in a sub-optimal solution. Conventional methods of pixelwise template matching thus suffer from high computation costs related to detecting Laplacian extrema that largely negate the benefits of LBP. Conventional methods of MsLBP also under-emphasize salient patterns while over-emphasizing insignificant patterns. Unsupervised hashing methods can lead to results no better than random binarization, while conventional supervised hashing is forced to relax the objective function due to the non-differentiable sign function. Conventional methods of pixelwise template matching thus suffer from high computation costs and inaccuracies that render them less than optimal for assessing MR images of a section of tissue taken from a CaP patient.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
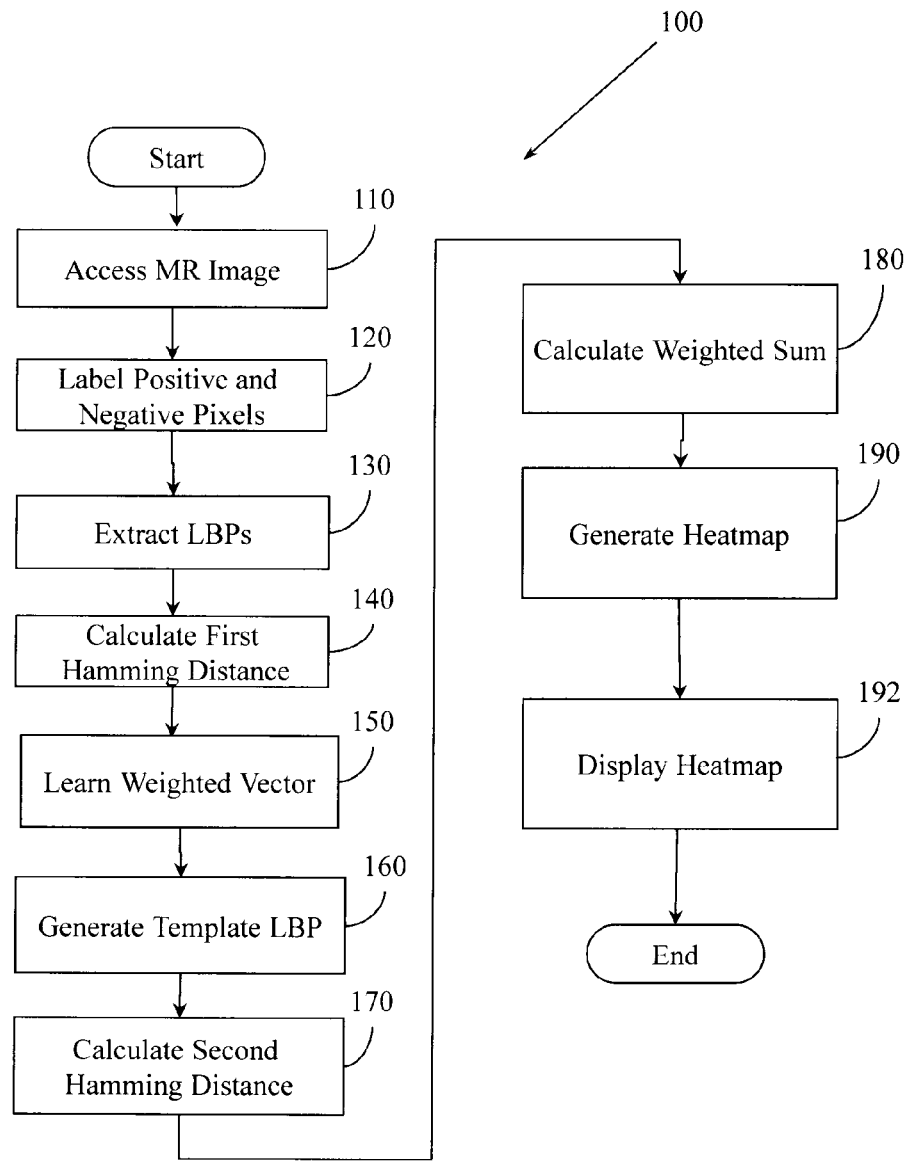
FIG. 1 illustrates an example method associated with detecting prostate cancer (CaP) in a magnetic resonance (MR) image of a prostate of a CaP patient.

Pixelwise template matching is commonly used to exhaustively search an image to find pixels similar to a query pixel. When investigating CaP in cancer patients, a query pixel may be a pixel deemed by a pathologist or other expert to represent a cancerous region of an image of a prostate. One of the challenges when matching pixels is the conflict between matching speed and accuracy. Ideally, pixel representation should be distinctive and compact, and computing its dissimilarity metric should be achievable in a clinically relevant timeframe. Conventional methods often employ LBP to match one pixel with another. The LBP descriptor of a pixel is a string of binary bits obtained by comparing the gray value of a pixel with the gray values of a number of other pixels sampled on a ring centered on the pixel. The Hamming distance of LBP refers to the number of bits that are different, and may be calculated using only bitwise XOR operations that are relatively computationally inexpensive. To extract salient LBP descriptors, a useful radius for the ring must be found. Conventional methods that detect Laplacian extrema are computationally expensive, which negates the benefits of LBP. Sampling multiple radii can statistically insure measuring textural content at a salient scale. By assuming independent sampling, measuring MsLBP is defined as the sum of the Hamming scores across a plurality of scales. Example apparatus and methods improve on conventional methods of combining the Hamming scores of LBPs at different scales. Example apparatus and methods define a weight vector to account for the statistical significance of information at the salient scale by measuring the dissimilarity between a pair of MsLBPs.

Conventional methods for indexing large image collections based on content employ learned binary projections. Unsupervised hashing in conventional methods, however, leads to binary codes that are frequently as poor as random binarization. Supervised hashing employed in conjunction with supervised learning explicitly learns a mapping that maximizes the distance among different classes. For example, one class may represent pixels sampled from a cancerous region and another class may represent non-cancerous pixels. However, the non-differentiable sign function often forces relaxing the objective function, which results in a sub-optimal solution. Example apparatus and methods employ discriminatively weighted local binary patterns (DWLBP) to combine multi-scale Hamming scores for matching MsLBP. In one embodiment, a weight vector is learned by minimizing the squares of Hamming distances between positive class samples and by jointly maximizing the Hamming distances between positive and negative class samples. Since elements of the resulting vector are normalized so that the sum of the elements equals one, example apparatus and methods may generate an objective function that is both convex and constrained by linear equality and inequality constraints. In one embodiment, the interior point method may be used to solve the objective function.

Example apparatus and methods employ supervised learning to optimally weigh the significance of multiple scales when combining Hamming scores. Example apparatus and methods yield a more general approach than the ad hoc approach of conventional methods. The problem of non-differentiability that hampers conventional supervised hashing systems may be avoided by shifting binarization to an earlier step of LBP extraction. Example apparatus and methods may produce a smooth, differentiable, and globally convex problem, which improves on conventional methods.

In one embodiment, two stages may be employed. The first stage is a learning procedure. T2 weighted MRI images of a prostate are analyzed and labelled with positive and negative samples. Positive samples may represent, for example, cancerous regions, while negative samples may represent non-cancerous regions. Given the labelled samples, multi-scale LBPs are extracted from the pixels in the image. The Hamming scores for the pixels are then computed at the different scales. The learning procedure concludes by learning a weight that optimally combines the multi-scale Hamming scores. In one embodiment, an optimal weight is a weight by which positives and negatives are separated as far as possible.

The second stage involves salient feature detection. Example apparatus and methods select a small number of distinct image pixels as template pixels. The LBP codes pertaining to the template pixels are extracted. An exhaustive search of the image area is then performed to match the LBPs of the pixels with the template LBPs at the different scales. A weighted sum of the Hamming scores of the different scales yields a statistical probability heatmap. Co-ordinates of the heatmap having higher probabilities, or hotter co-ordinates, indicate candidate salient features.

LBP operates on the intensity values of image pixels and models a single pixel via its local neighbors. For an arbitrary pixel with an intensity value $f_c$, the LBP number of the arbitrary pixel consists of the signs of the gray-level value discrepancies between $f_c$ and the gray-level values of p equally spaced pixels on a circle of radius $x=\Sigma_{i=0}^{p-1} \text{sign}(f_i-f_c)2^i$ in a digitized MR image, where p is an integer. In this example, $f_i$, $i\in\{0, 1, \ldots, p-1\}$ is the gray-level intensity value of an $i^{th}$ sampled pixel. The sign function sign is defined as $$\text{sign}(y) = \begin{cases} 1, & \text{if } y \geq 0; \\ 0, & \text{if } y < 0. \end{cases}$$

The co-ordinates of $f_i$ are given by $$\left(-r\sin\left(\frac{2\pi i}{p}\right), r\cos\left(\frac{2\pi i}{p}\right)\right).$$

The $f_i$ taken together form a circularly symmetric neighbor set where r is the radius of the circle. The binomial factor $2^i$ transforms the LBP to a number whose bits are measured in Hamming distance. LBP is, by definition, invariant to local gray-scale shift. However, in order for LBP to be rotation-invariant, a circular bitwise right shift on the p bits is performed p times. The minimum resulting number from the circular bitwise right shift is retained as the final LBP output.

Example apparatus and methods employ multi-scale linear binary patterns (MsLBP). By combining multiple operators by varying the number of pixels and the radius (p, r), an LBP may capture the property of multi-resolution textures. The metric for measuring a similarity between a pair of multiscale LBPs is through a simple kernel defined as $H(x, x')=\Sigma_{n=1}^{N} d_H(x_n, x_n')$. In this example, N is a number of operations of varying (p, r). The Hamming distance is defined as $d_H(x_n, x_n')$, where $d_H=\Sigma_{i=0}^{p_n-1}(x_i \neq x_i')$. In this example, $x_i$ is the $i^{th}$ bit of x, and $x_i'$ is the $i^{th}$ bit of x'.

While the dissimilarity measured by LBP assigns a uniform weight to each scale, example apparatus and methods employ a general scale selection scheme that learns a weight $w\in[0, 1]$ for the different scales. Consider an LBP example that involves N operations by altering (p, r). In one embodiment a vector $w\in R^{N\times 1}$ is sought such that the dissimilarity metric becomes a weighted sum. The weighted sum is defined as $H(x, x')=\Sigma_{n=1}^{N} w_n d_H(x_n, x_n')=w^T b_H$, where $w\in[0,1]$ is a weight for a scale in a plurality of scales. In this example, $b_H$ is a column vector of $d_H(x_n, x_n')$.

Example apparatus and methods learn an optimal vector w from a non-empty set P of positive LBP descriptors extracted from representative positive sample pixels and a non-empty set N of negative LBP descriptors extracted from representative negative sample pixels. Example apparatus and methods may simultaneously minimize the weighted Hamming distances between the samples of P (the intra-class distance) and maximize the Hamming distances of samples between P and N (the inter-class distance). In one embodiment, an objective function is minimized to find w. The objective function is defined as $\min_w \Sigma_{x\in P, x'\in P} H^2(x, x') - \alpha \Sigma_{x\in P, x'\in N} H^2(x, x')$, such that $1 \geq w_n \geq 0$, $n=1, \ldots, N$, and $\Sigma_{n=1}^{N} w_n = 1$. In one embodiment, $\alpha$ balances the intra-class and inter-class distances. $1 \geq w_n \geq 0$ constrains that $w_n$ is a weight and that $w_n$ satisfies $\Sigma_{n=1}^{N} w_n = 1$.

Example apparatus and methods may combine the weighted sum and the objective function. The combination of the objective function and the weighted sum yields $\Sigma_{x \in P, x' \in P} w^T b_H b_H^T w - \alpha \Sigma_{x \in P, x' \in PN} w^T b_H b_H^T w = w^T \Sigma_P w - \alpha w^T \Sigma_{PN} w$. In this example, $\Sigma_P = \Sigma_{x \in P, x' \in P} b_H b_H^T$ is the intra-class Hamming distance, and $\Sigma_{PN} = \Sigma_{x \in P, x' \in N} b_H b_H^T$ is the inter-class Hamming distance. Example apparatus and methods may arrange the combination of the objective function and the weighted sum into a matrix form: $\min_w w^T (\Sigma_P - \alpha \Sigma_{PN}) w$ such that $b^T w = 1$ and $0 \leq w \leq 1$. In this example, $b = [1, \ldots, 1]^T$, $b \in R^{N \times 1}$, and $\Sigma_P - \alpha \Sigma_{PN}$ is symmetric. $\min_w w^T (\Sigma_P - \alpha \Sigma_{PN}) w$ is a quadratic function with both linear equality and inequality constraints. Example apparatus and methods may choose $\alpha$ to keep $\Sigma_P - \alpha \Sigma_{PN}$ positive definite. Since the two constraints are both convex set, example apparatus and methods yield a convex optimization problem. In one embodiment, the convex optimization problem is solved using the interior point optimization method. An example of the interior point optimization method is implemented by the MATLAB quadprog function.

Example apparatus and methods may operate on direct binary strings and learn a weight vector. Recall that conventional learning-based hashing techniques employ a projection matrix. Example apparatus and methods improve on conventional methods by reducing the computation cost in computing $\Sigma_P$ and $\Sigma_{PN}$ with bitwise comparisons. Example apparatus and methods further improve on conventional methods by eliminating the problems associated with the non-differentiable binary function. By learning appropriate weights, example apparatus and methods apply the weighted Hamming metric found with the weighted sum to index an entire image surface with a chosen query pixel. When applied to CaP diagnosis, example apparatus and methods improve the accuracy of cancer prediction compared to conventional methods. In one embodiment, an area value under ROC curve (AUC) may be achieved that is on average 1.25% larger than conventional methods when distinguishing between cancerous and benign regions on a per pixel basis.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a method 100 associated with detecting prostate cancer (CaP) in a magnetic resonance (MR) image of a prostate of a CaP patient. Method 100 includes, at 110, accessing a digitized MR image of the prostate. The digitized MR image includes a set of pixels and gray-level intensity information about the pixels. In one embodiment, the digitized MR image is a T2 weighted MRI image. In one example, the digitized MR image has a size of 512 pixels by 512 pixels. Other weighted images with other pixel sizes may be employed.

Method 100 also includes, at 120, labelling one or more cancerous pixels in the digitized MR image as positive and labelling one or more benign pixels in the digitized MR image as negative. In one embodiment, method 100, at 120, produces a set of positive pixels P and a set of negative pixels N. In one embodiment employing supervised learning, a pathologist or other expert may label the one or more cancerous pixels as positive the one or more benign pixels as negative.

Method 100 also includes, at 130, extracting a local binary pattern (LBP) for a cancerous pixel in the one or more cancerous pixels. In one embodiment, LBPs are extracted for the one or more cancerous pixels at a plurality of scales. Method 100 also includes, at 130, extracting LBPs of a benign pixel in the one or more benign pixels. The LBPs extracted from the benign pixel are also extracted at a plurality of scales. In one embodiment, an LBP comprises an LBP number. The LBP number may include the signs of a gray-level intensity value discrepancy between a gray-level intensity value of a first pixel from the digitized MR image. The first pixel is represented by $f_c$. The LBP number may also include the gray-level intensity values of p equally spaced sampled pixels on a circle of radius $x = \Sigma_{i=0}^{p-1} \text{sign}(f_i - f_c) 2^i$ in the digitized MR image, where p is an integer. In one embodiment, $f_i$, $i \in \{0, 1, \ldots, p-1\}$ is the gray-level intensity value of an $i^{th}$ sampled pixel, and sign is a sign function defined as $$\text{sign}(y) = \begin{cases} 1, & \text{if } y \geq 0; \\ 0, & \text{if } y < 0. \end{cases}$$

In one embodiment, the co-ordinates of $f_i$ are given by $$\left( -r \sin\left(\frac{2\pi i}{p}\right), r \cos\left(\frac{2\pi i}{p}\right) \right).$$

The co-ordinates of $f_i$ within the circle together form a circularly symmetric neighbor set, in which r represents the radius of the circle. In one embodiment, r is fixed as $r \in \{4, 8, 12, 14, 16, 20, 24, 28, 32, 36\}$. In one embodiment, the number of sample pixels p is obtained from $p \in \{8, 16, 32, 64\}$. In one embodiment, LBP patterns at scales $r \in \{8, 12, 14, 16\}$ are less discriminating than LBP patterns obtained at scales $r \in \{4, 20, 24, 28, 32, 36\}$, indicating that small and large scales tend to be more discriminating than medium scales.

Method 100 also includes, at 140, calculating a first Hamming distance for the one or more cancerous pixels and the one or more benign pixels at the plurality of scales. In one embodiment, the binomial factor $2^i$ used in the equation $x=\Sigma_{i=0}^{p-1}\text{sign}(f_i-f_c)2^i$ transforms the LBP to a number. In this example, the bits of the number are measured in Hamming distance. By definition, the LBP is invariant to local gray-scale shift. A circular bitwise right shift is performed p times on p bits within the circle, and the minimum resulting number of the circular bitwise right shift is retained as the final LBP. Other manipulations may be performed in other embodiments. In one embodiment, calculating the first Hamming distance includes, at 140, finding a similarity between a pair of LBPs at the plurality of scales. The similarity is computed as a dissimilarity metric. The dissimilarity metric may be measured by a kernel defined as $H(x, x')=\Sigma_{n=1}^{N} d_H(x_n, x_n')$. In this example, N is a number of operations of varying the number of sample pixels and the radius (p, r). Here, $d_H(x_n, x_n')$ is the Hamming distance, where $d_H=\Sigma_{i=0}^{P\cdot r-1}(x_i \neq x_i')$. The $i^{th}$ bit of x is represented by $x_i$, and $x_i'$ represents the $i^{th}$ bit of x'.

Calculating the first Hamming distance may also include computing a dissimilarity metric. In one embodiment, the dissimilarity metric is a weighted sum defined as $H(x, x')=\Sigma_{n=1}^{N} w_n d_H(x_n, x_n')=w^T b_H$. In this embodiment, $w \in [0,1]$ is a weight for a scale in the plurality of scales, where $w \in R^{N \times 1}$. In one embodiment, $b_H$ is a column vector of $d_H(x_n, x_n')$.

Method 100 also includes, at 150, learning a weighted vector w that weighs the first Hamming distance at the plurality of scales. In one embodiment, learning a vector includes calculating a minimized objective function $\min_w \Sigma_{x \in P, x' \in P} H^2(x, x')-\alpha \Sigma_{x \in P, x' \in P} H^2(x, x')$, such that $1 \geq w_n \geq 0$, $n=1, \ldots, N$, and $\Sigma_{n=1}^{N} w_n=1$. In one example, P is a subset of the one or more cancerous pixels in the digitized MR image classified as positive, and N is a subset of the one or more non-cancerous pixels in the digitized MR image classified as negative. In this example, $\alpha$ balances an intra-class Hamming distance and an inter-class Hamming distance. The constraint $1 \geq w_n \geq 0$ constrains that $w_n$ is a weight and that $w_n$ satisfies $\Sigma_{n=1}^{N} w_n=1$.

Method 100 further includes when learning a vector, at 150, combining the weighted sum with the minimized objective function. Combining the weighted sum with the minimized objective function results in $\Sigma_{x \in P, x' \in P} w^T b_H b_H^T w - \alpha \Sigma_{x \in P, x' \in N} w^T b_H b_H^T w = w^T \Sigma_P w - \alpha w^T \Sigma_{PN} w$, where $\Sigma_P = \Sigma_{x \in P, x' \in P} b_H b_H^T$ is the intra-class Hamming distance, and $\Sigma_{PN} = \Sigma_{x \in P, x' \in N} b_H b_H^T$ is the inter-class Hamming distance. The intra-class Hamming distance is based on the sum of the set P and the inter-class Hamming distance is based on the sum of the sets PN. Method 100, at 150, also arranges the combined weighted sum and minimized objective function into matrix form as $\min_w w^T (\Sigma_P - \alpha \Sigma_{PN}) w$ such that $b^T w=1$ and $0 \leq w \leq 1$. In this example, $b=[1, \ldots, 1]^T$, $b \in R^{N \times 1}$. The matrix $\Sigma_P - \alpha \Sigma_{PN}$ is a symmetric matrix. In one embodiment $\alpha$ is chosen to keep $\Sigma_P - \alpha \Sigma_{PN}$ positive definite. In one embodiment, the performance of method 100 is robust to changes in $\alpha$, in which $\alpha$ varies among 0.01, 0.04, 0.08, 0.1, 0.12, and 0.2. In one embodiment, method 100 employs interior-point optimization to solve the minimized objective function. Learning a vector results in the weighted vector w.

Method 100 also includes, at 160, generating a template LBP. Generating a template LBP may include extracting an LBP from a template pixel selected from a non-empty subset of the set of pixels. In one embodiment, the template pixel is selected manually by a pathologist or other expert. In another embodiment, the template pixel is automatically selected.

Method 100 also includes, at 170, calculating second Hamming distances of the template LBP and of the LBP of a pixel other than the template pixel. The second Hamming distances are calculated at the plurality of scales. In one embodiment, the plurality of scales is defined by the radius r of the circle, where $r \in \{4, 8, 12, 14, 16, 20, 24, 28, 32, 36\}$. In another embodiment, r may be selected from a different set of radii, resulting in a different plurality of scales.

Method 100 also includes, at 180, calculating a weighted sum of the second Hamming distances at the plurality of scales as a function of the second Hamming distances and the weighted vector w. In one embodiment, calculating the weighted sum of the second Hamming distances at the plurality of scales as a function of the second Hamming distances and the weighted vector w includes computing $w^T b_H$.

Method 100 also includes, at 190, generating a statistical probability heatmap based, at least in part, on the weighted sum. In one embodiment, the co-ordinates of the heatmap with higher probability indicate a higher probability that a region of the prostate corresponding to the co-ordinate is cancerous. Similarly, co-ordinates of the heatmap with lower probability indicate a lower probability that a region of the prostate corresponding to the co-ordinate is cancerous. In one embodiment, hotter regions of the heatmap indicate regions of higher probability and cooler regions of the heatmap indicate regions of lower probability. In one embodiment, cancer ground-truth may be displayed as red. In another embodiment, a graphical display other than a heatmap suitable for displaying information contained in a matrix may be employed to indicate the statistical probabilities based, at least in part, on the weighted sum. For example, a gray-scale map or a surface plot may be employed.

Method 100 also includes, at 192, displaying the statistical probability heatmap to facilitate distinguishing between cancerous and benign tissue on a per-pixel basis. In one embodiment, a color bar located adjacent to the heatmap indicates the suspected probability of any pixel in the image representing a cancerous region of tissue. In one embodiment, the heatmap may be displayed on a computer monitor. In another embodiment, the heatmap may be printed.

While FIG. 1 illustrates various actions occurring in serial, it is to be appreciated that various actions illustrated in FIG. 1 could occur substantially in parallel. By way of illustration, a first process could extract positive pixels from an MR image, a second process could extract LBPs associated with the positive pixels, and a third process could extract negative pixels from the MR image. While three processes are described, it is to be appreciated that a greater or lesser number of processes could be employed and that lightweight processes, regular processes, threads, and other approaches could be employed.

Figure 2:
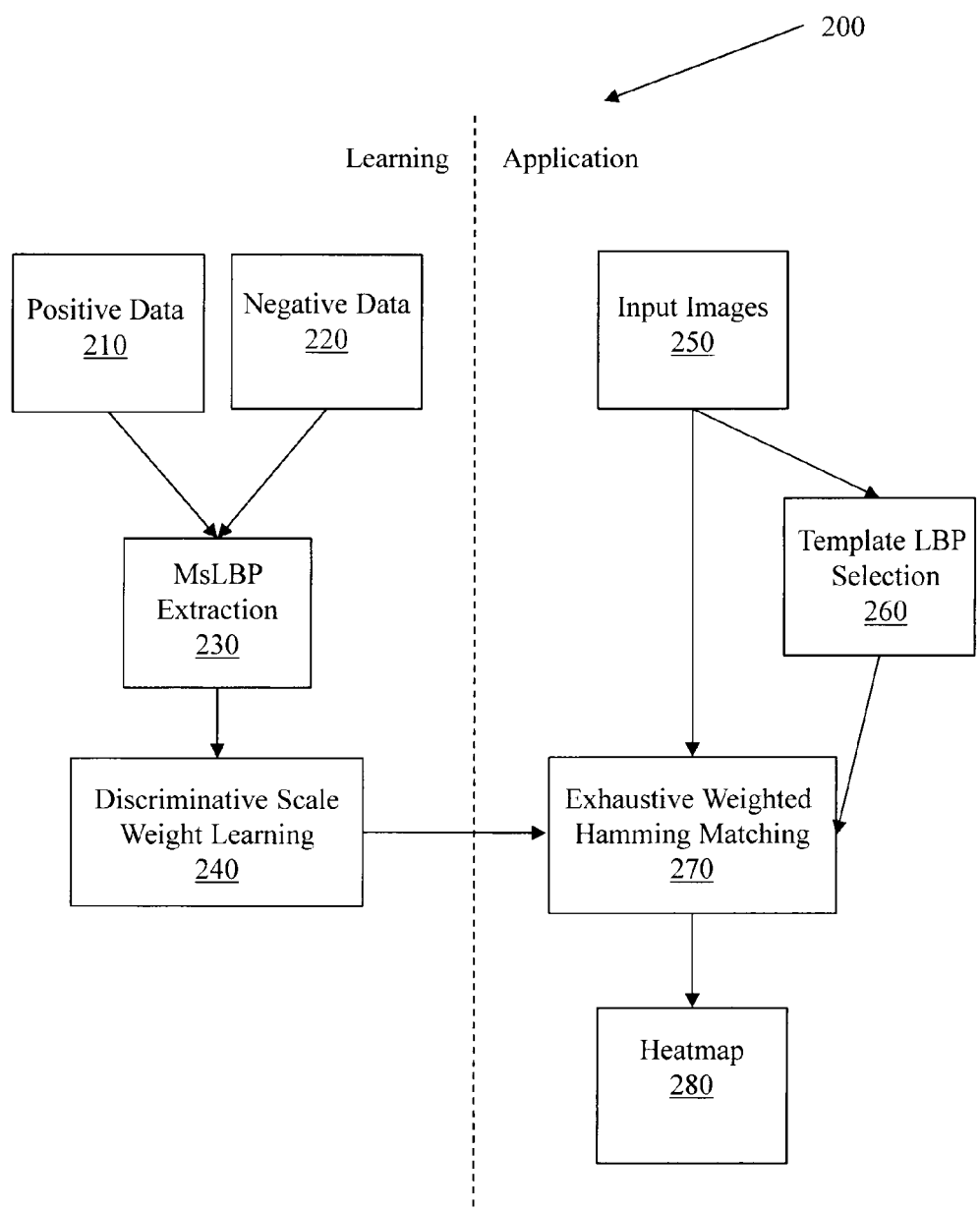
FIG. 2 illustrates a flow chart for detecting CaP in an MR image of a prostate of a CaP patient.

FIG. 2 is a flowchart of a two-stage procedure for detecting prostate cancer (CaP) in a magnetic resonance (MR) image of a prostate of a CaP patient. The first stage, illustrated on the left side of FIG. 2, is the learning procedure. Class sample 210 represents positive pixels sampled from an MR image of a prostate. Class sample 220 represents negative pixels sampled from the MR image of a prostate. FIG. 2 illustrates, at 230, the extraction of multi-scale LBP codes from the positive class sample 210 and from the negative class sample 220. At 240, the MsLBP codes are used to discriminatively train an optimal vector. The optimal vector weighs the Hamming score of the pixels at each scale. In one embodiment, the optimal vector is passed from the learning procedure to the application procedure. The second stage, illustrated on the right side of FIG. 2, is the application procedure. An input image 250 (or images) of a prostate are provided to template LBP selection 260. The template LBP selection 260 may be, for example, iterative. The input image 250 is also provided to exhaustive weighted Hamming matching 270. In one embodiment, the exhaustive weighted Hamming matching 270 may be performed over the entire input image. While FIG. 2 illustrates exhaustive weighted Hamming matching over the entire input image, it will be appreciated that in various embodiments, not all of the pixels in an image need to be searched. While for a 512 pixel by 512 pixel image comprising 262,144 pixels, searching all 262,144 pixels may produce an optimal result, searching 260,000 pixels, or 200,000 pixels may also produce a useful result. FIG. 2 also illustrates a heatmap 280 that may be generated based, at least in part, on the similarity between the discriminatively weighted LBP scores between the template pixels and the pixels searched over the image.

Figure 3:
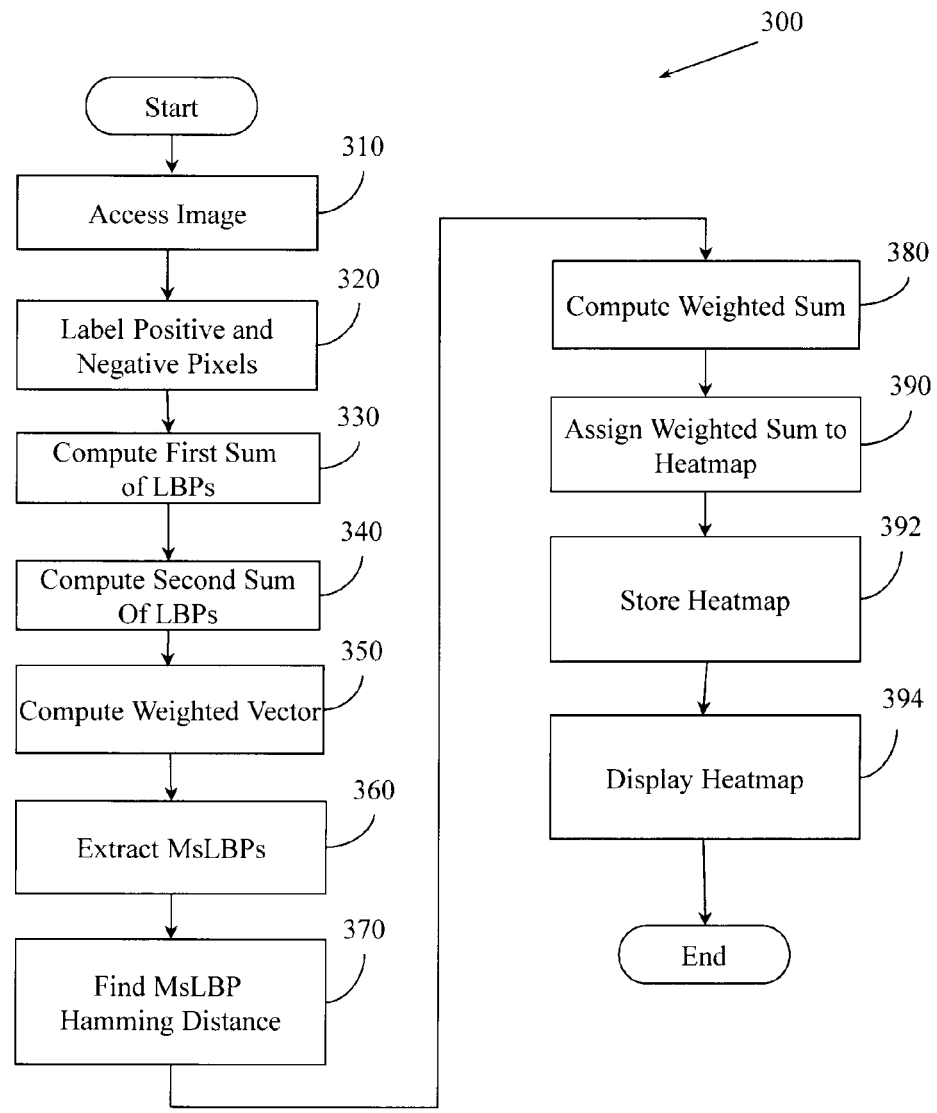
FIG. 3 illustrates an example method for generating and displaying a statistical probability heatmap based on a weighted vector learned from a set of positive pixels and a set of negative pixels.

FIG. 3 illustrates a method 300 associated with generating and displaying a statistical probability heatmap based on a weighted vector learned from a set of positive pixels and a set of negative pixels. Method 300 includes, at 310, accessing a digitized image of a region of interest. In one embodiment, the digitized image is an image of a prostate. In another embodiment, the digitized image is an image of a region of interest of a tissue that may be cancerous. In another embodiment, the digitized image is of a region of interest in a material that exhibits binary properties suitable for analysis with LBP. While cancerous and non-cancerous regions are described in relation to example apparatus and methods, it will be appreciated that materials that exhibit binary properties, and in which the probability that a region of the material is negative or positive may be analyzed by a statistical probability heatmap, may be analyzed using example apparatus and methods.

Method 300 also includes, at 320, labelling a non-empty subset of pixels in the input image as a positive set. In one embodiment, pixels determined by a pathologist or other expert to represent cancerous regions of a prostate are labelled as positive. Method 300, at 320, also includes labelling a non-empty subset of pixels in the input image as a negative set. In one embodiment, non-cancerous, benign regions of the image are labelled as negative. The negative set does not include the positive set. The positive set may be referred to as P and the negative set may be referred to as N.

Method 300 also includes, at 330, computing a first sum of positive local binary pattern (LBP) descriptors as a function of the positive set. In one embodiment, the first sum is referred to as $\Sigma_P$. Method 300, at 340, also includes computing a second sum of negative and positive LBP descriptors as a function of the negative set and the positive set. In one embodiment, the second sum is referred to as $\Sigma_{PN}$.

Method 300 also includes, at 350, computing a weighted vector from the first sum of positive LBP descriptors $\Sigma_P$ and the second sum of negative and positive LBP descriptors $\Sigma_{PN}$. In one embodiment, computing the weighted vector includes computing a weighted vector w. Computing the weighted vector w includes optimizing $\min_w w^T(\Sigma_P - \alpha\Sigma_{PN})w$ such that $b^T w=1$ and $0 \le w \le 1$, where $b=[1, \ldots, 1]^T$, $b \in R^{N \times 1}$. In this example, P is the first sum, PN is the second sum, and $\Sigma_P - \alpha\Sigma_{PN}$ is a symmetric matrix. In this example, $\alpha$ is chosen to keep $\Sigma_P - \alpha\Sigma_{PN}$ positive definite. N is a number of operations of varying (p, r), where p is a set of equally spaced pixels of the input image on a circle having radius r.

Method 300 also includes, at 360, extracting a multiscale LBP at a co-ordinate of the input image at a plurality of scales. In one embodiment, the co-ordinates of the input image are represented by Cartesian co-ordinates in which i indicates the x co-ordinate and j indicates the y co-ordinate. In this example, at 360, method 300 scans the image at each position (i, j) and extracts multiscale LBPs at each position. In another embodiment, method 300 scans the image at less than each position (i, j), for example, scanning only odd numbered rows and odd numbered columns. It will be appreciated that while scanning each position may produce an optimal result, scanning less than each position may still produce clinically useful results as part of the tradeoff between computational speed and accuracy. In one embodiment, the plurality of scales is based on the set of radii $r \in \{4, 8, 12, 14, 16, 20, 24, 28, 32, 36\}$. In another embodiment, other radii may be chosen.

Method 300 also includes, at 370, finding the Hamming distance of the multi-scale LBP at the plurality of scales. In one embodiment, the Hamming distance is defined as $d_H(x_n, x_n')$, where $d_H = \Sigma_{i=0}^{Pn-1}(x_i \ne x_i')$. In one embodiment, the Hamming distance of the multi-scale LBP is computed for each position (i, j) as $d_H(x_{ij}'', x_0'')$, where $x_0''$ represents the query pixel. In another embodiment, the Hamming distance of the multi-scale LBP is computed for less than each position (i, j).

Method 300 also includes, at 380, computing a weighted sum as a function of the transpose of the weighted vector and a column vector of the Hamming distance of the multiscale LBP. In one embodiment, computing the weighted sum includes computing $w^T b_H = \Sigma_{n=1}^{N} w_n d_H(x_n, x_n') = H(x, x')$. In one embodiment, $d_H(x_n, x_n')$ is the Hamming distance, where $d_H = \Sigma_{i=0}^{Pn-1}(x_i \ne x_i')$. In this example, $x_i$ is the $i^{th}$ bit of x, and $x_i'$ is the $i^{th}$ bit of x'.

Method 300 also includes, at 390, assigning the weighted sum for the co-ordinate to a statistical probability heatmap of the input image. In one example, where the heatmap is represented as $\Theta(f)$, the weighted sum is assigned to $\Theta(f)$ at the positions (i, j) scanned by blocks 360 and 370.

Method 300 also includes, at 392, updating a memory to store the statistical probability heatmap. In one embodiment, the memory may include a random access memory (RAM), a memory chip or card, a memory stick, and other media from which a computer, a processor or other electronic device can read.

Method 300 also includes, at 394, controlling a display to display the statistical probability heatmap. In one embodiment, the statistical probability heatmap facilitates distinguishing regions of the input image associated with the positive set and regions of the input image associated with the negative set. The display may include, for example, a computer monitor, a smartphone display, a tablet display, or other displays. Displaying the statistical probability heatmap may also include printing the heatmap. In one embodiment, the statistical probability heatmap is a heatmap. In another embodiment, the statistical probability heatmap may be displayed as a combination of a heatmap and a surface plot, or other type of display suitable for representing individual values stored in elements of a matrix.

Figure 4:
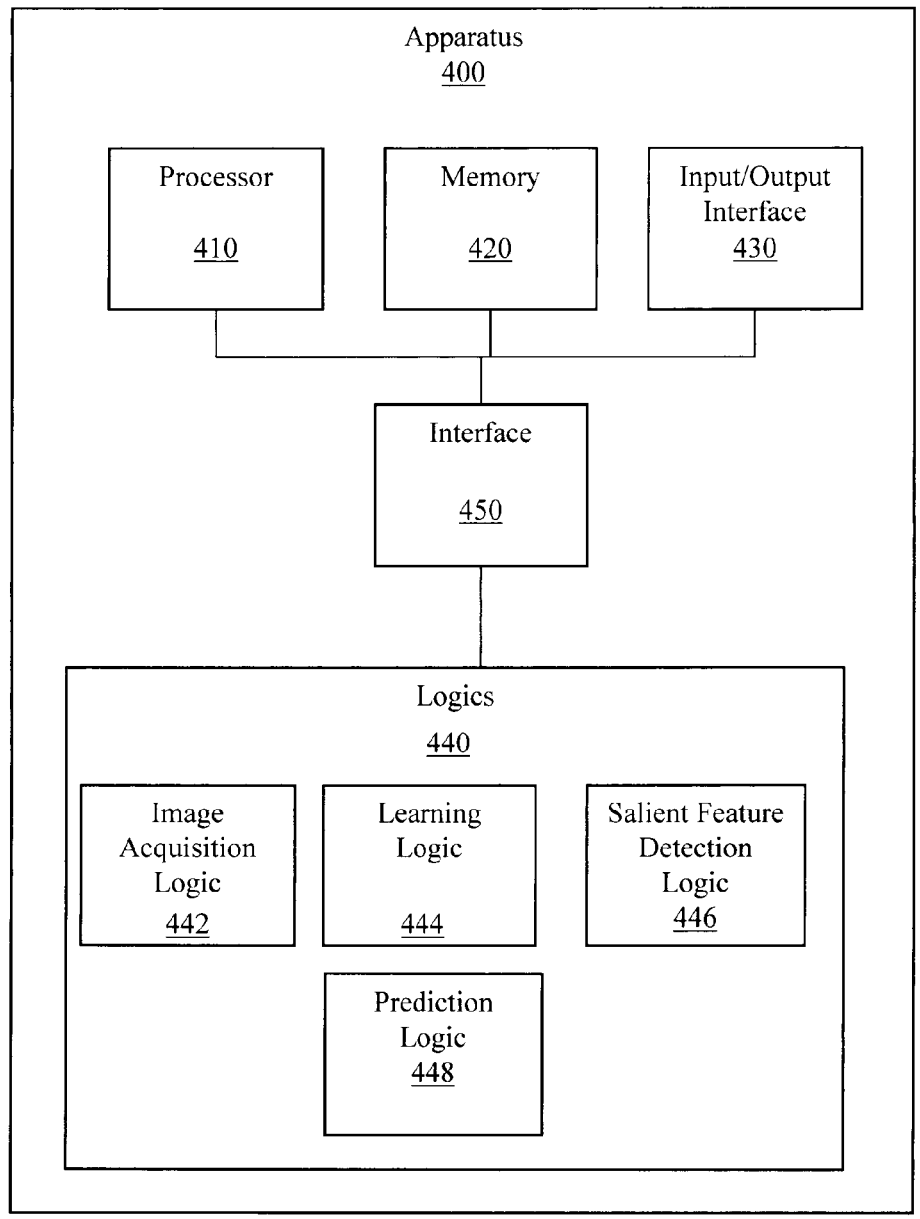
FIG. 4 illustrates an example apparatus associated with predicting cancer.

FIG. 4 illustrates an example apparatus 400. Apparatus 400 includes a processor 410, a memory 420, an input/output interface 430, a set of logics 440, and an interface 450 to connect the processor 410, the memory 420, the input/output interface 430, and the set of logics 440. In one embodiment, the set of logics 440 learns a weighted vector, detects salient features in an image, and generates a statistical probability heatmap suitable for use in predicting the probability a region of a prostate is cancerous.

The set of logics 440 learns a weighted vector based on LBPs extracted from a set of positive pixels and set of negative pixels, detects salient features in an image, based, at least in part, on the weighted vector, and generates a statistical probability heatmap suitable for use in predicting the probability a region of a prostate is cancerous, based in part on the weighted vector. The set of logics 440 may include an image acquisition logic 442 that acquires one or more images of a tissue. In one embodiment, the one or more images are T2 weighted MRI images.

The set of logics 440 may also include a learning logic 444 that extracts a set of positive salient feature sample pixels from a magnetic resonance (MR) image of a region of tissue, extracts a set of negative non-salient feature pixels from the image, extracts multiscale local binary pattern (MsLBP) codes from the set of positive sample pixels and the set of negative sample pixels, and computes a weighted vector by discriminatively training a vector that weighs the Hamming value of a pixel at a plurality of scales. In one embodiment, the weighted vector is computed according to $\min_w w^T (\Sigma_P - \alpha \Sigma_{PN}) w$ such that $b^T w = 1$ and $0 \leq w \leq 1$, where $b = [1, \ldots, 1]^T$, $b \in R^{N \times 1}$.

The set of logics 440 may also include a salient feature detection logic 446 that selects a template pixel from the image, searches over the image to match the local binary pattern (LBP) of a pixel in the image with the LBP of the template pixel at a plurality of scales, finds the Hamming distance for the pixel at a plurality of scales, and computes a weighted sum as a function of the weighted vector and a column vector of the Hamming distance. In one embodiment, salient feature detection logic 446 iteratively selects the template pixel. In one embodiment the salient feature detection logic 446 searches over the entire image space. In another embodiment, the salient feature detection logic 446 searches over less than the entire image space.

The set of logics 440 may also include a prediction logic 448 that generates a statistical probability heatmap based, at least in part, on the weighted sum. In the heatmap, hotter regions have a higher probability of indicating a salient feature, and cooler regions of the heatmap have a lower probability of indicating a salient feature. In one embodiment, the heatmap is a heatmap. In another embodiment, the heatmap may be a combination of a surface plot and a heatmap. In one embodiment, prediction logic 448 may control a computer to display the heatmap on a monitor. In another embodiment, a hardcopy of the heatmap may be printed.

Figure 5:
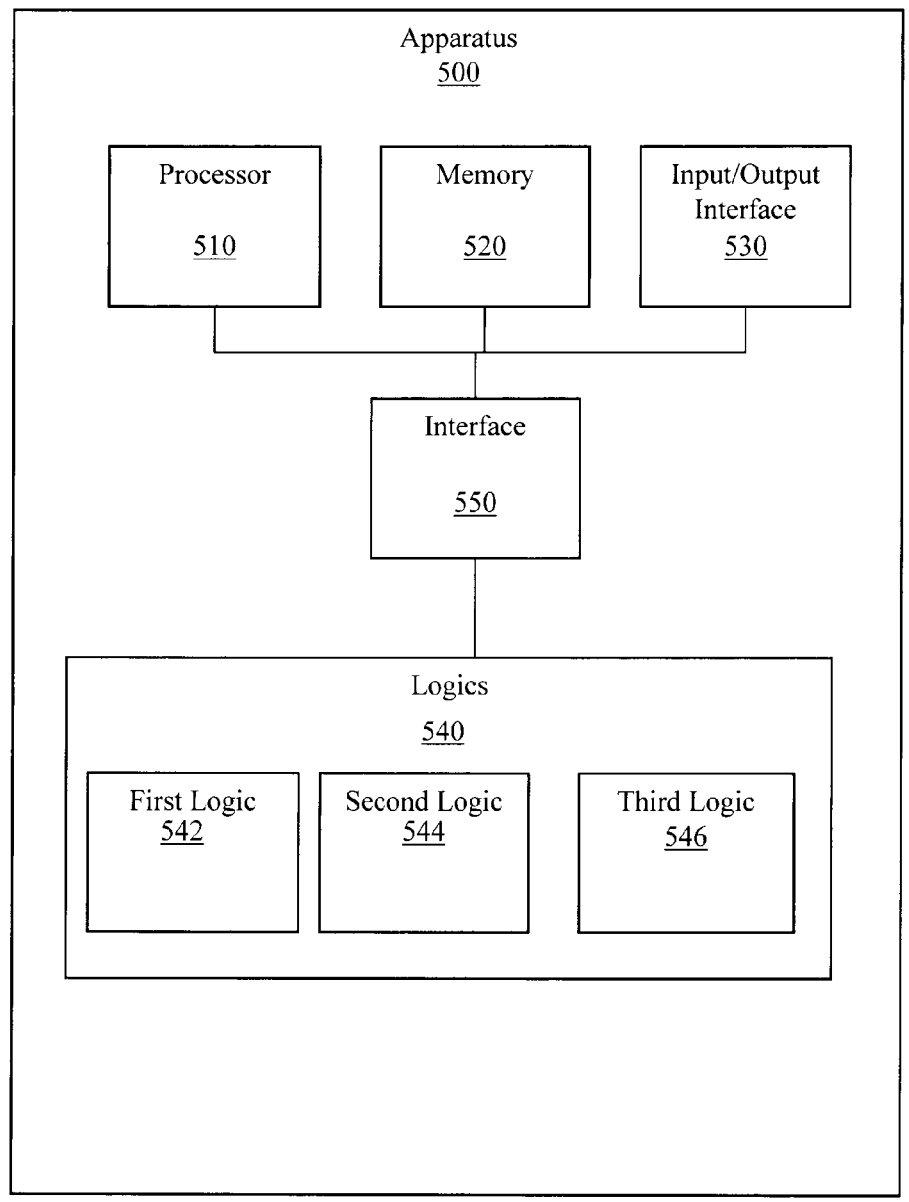
FIG. 5 illustrates an example apparatus associated with predicting cancer.

FIG. 5 illustrates an example apparatus 500 associated with predicting cancer. Embodiments of apparatus 500 may be employed to evaluate salient features in a region of a material in which positive cancerous tissue is identified and negative non-cancerous tissue is identified. Embodiments of apparatus 500 may learn a weighted vector based on pixels in an image corresponding with the positive and negative identified tissue, may determine a similarity between a template pixel and another pixel in the image, and may facilitate predicting cancer by producing a heatmap of the image based, at least in part, on the weighted vector and the similarity. Apparatus 500 includes a first logic 510 that generates a weighted vector. Apparatus 500 also includes a second logic 520 that determines a similarity between a template pixel and another pixel in an image, at least in part, on the weighted vector. Apparatus 500 also includes a third logic that facilitates predicting cancer by producing a heatmap of the image based, at least in part, on the weighted vector and the similarity.

First logic 510 generates a weighted vector. First logic 510 acquires one or more images of a material. In one embodiment, the one or more images are of a prostate. In another embodiment, the material is a region of biological tissue other than prostate. In one embodiment, the images are T2 weighted MR images. In another embodiment, the images are 3D MRI images. First logic 510 identifies a set of positive representative samples. Positive representative samples are LBP descriptors extracted from pixels from the one or more images identified as being cancerous. First logic 510 computes a sum of the positive representative samples. First logic 510 identifies a set of negative representative samples. The set of negative representative samples are LBP descriptors extracted from pixels identified as being non-cancerous or benign. First logic 510 also computes a sum of the positive and negative samples. First logic 510 computes a weighted vector, based, at least in part, on the sum of the positive representative samples and the sum of the positive and negative representative samples. The weighted vector is learned by simultaneously minimizing the weighted Hamming distances between the positive representative samples and maximizing the Hamming distances between the positive and negative representative samples.

Second logic 520 determines a similarity between a template pixel and another pixel in an image based, at least in part, on the weighted vector. A template pixel is selected from the one or more images. In one embodiment, the template pixel may be selected manually by a pathologist or other skilled examiner. In another embodiment, the template pixel may be selected automatically. Second logic 520 scans the one or more images pixel by pixel. Second logic 520 extracts multiscale LBPs for the scanned pixels. Second logic 520 computes the Hamming distances of the scanned pixels and the template pixel at a plurality of scales. In one embodiment, the plurality of scales is defined by the radii of circles centered on the template pixel, where the radii is fixed as $r \in \{4, 8, 12, 14, 16, 20, 24, 28, 32, 36\}$. In one embodiment, optimally discriminating results are achieved using $r \in \{4, 20, 24, 28, 32, 36\}$. In another embodiment, other radii may be employed. Second logic 520 computes a weighted sum based in part on the transpose of the weighted vector and a column vector of the Hamming distance.

Third logic 530 facilitates predicting cancer by producing a heatmap of the one or more images based, at least in part, on the weighted vector and the similarity. Third logic 530 assigns the weighted sum computed by second logic 520 to a heatmap at the co-ordinates at which second logic 520 determined the similarity. Thus, a weighted sum computed for co-ordinates (i, j) would be assigned to the heatmap also at co-ordinates (i, j). In one embodiment, the heatmap is a statistical probability heatmap in which hotter regions indicate a higher probability that the region is cancerous and cooler regions indicate a lower probability that the region is cancerous. In one embodiment, a color bar shows the suspected probability of regions in the heatmap being cancerous. In another embodiment, a heatmap may be combined with a surface plot to facilitate predicting cancer. Third logic 530 displays the heatmap. In one embodiment, third logic 530 controls a computer to display the heatmap on a computer monitor. In another embodiment, third logic 530 displays the heatmap on a smartphone display, or a tablet computer display. Third logic 530 may also cause a hard copy of the heatmap to be printed.

Figure 6:
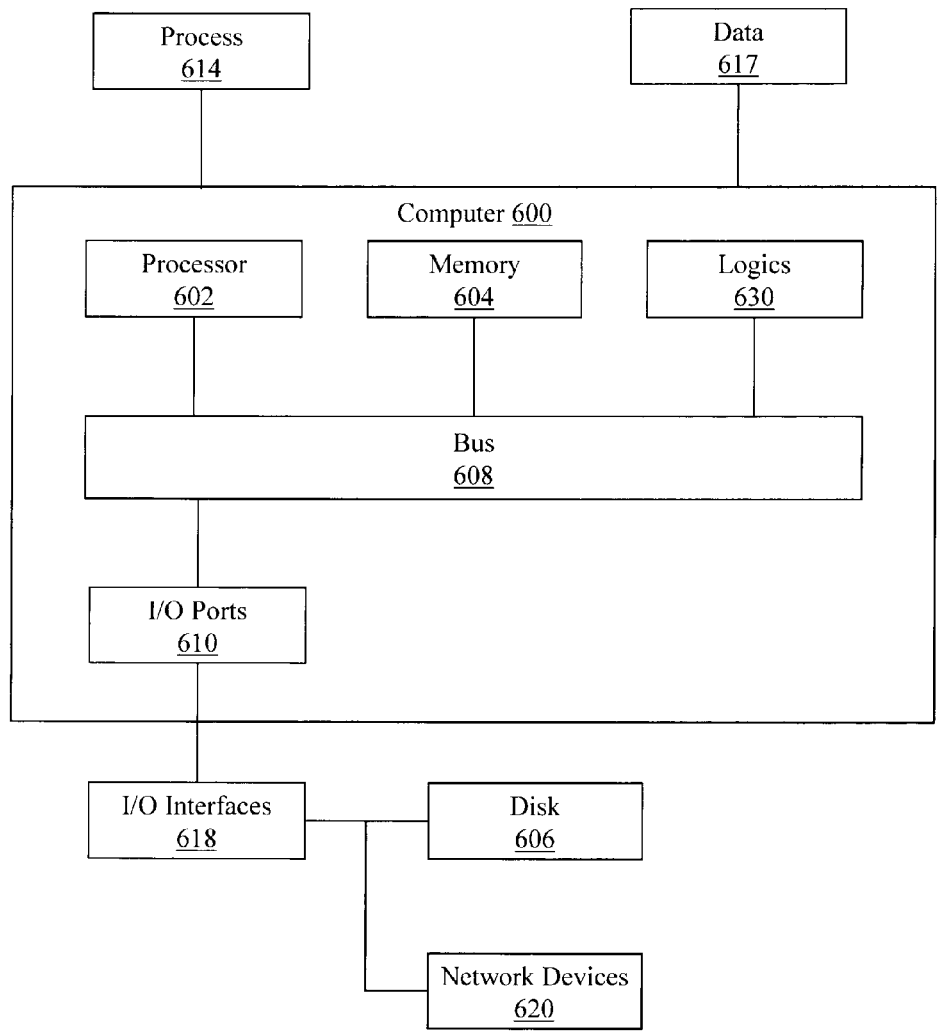
FIG. 6 illustrates an example computer 600 in which example methods illustrated herein can operate and in which example logics may be implemented.

FIG. 6 illustrates an example computer 600 in which example methods illustrated herein can operate and in which example logics may be implemented. In different examples computer 600 may be part of an MRI scanner or may be operably connectable to a MRI scanner that acquires MR images of a prostate or other region of tissue.

Computer 600 includes a processor 602, a memory 604, and input/output ports 610 operably connected by a bus 608. In one example, memory 604 is configured to store heatmaps. In one example, computer 600 may include a set of logics 630 that performs a method associated with detecting prostate cancer (CaP) in a magnetic resonance (MR) image of a prostate of a CaP patient. In another example, the set of logics 630 may control the computer 600 to generate a heatmap to facilitate predicting prostate cancer. Thus, the set of logics 630, whether implemented in computer 600 as hardware, firmware, software, or a combination thereof may provide means (e.g., hardware, software, circuit) for receiving digitized image data, means (e.g., hardware, software, circuit) for performing a method associated with detecting prostate cancer (CaP) in a magnetic resonance (MR) image of a prostate of a CaP patient, and means (e.g., hardware, software, circuit) for generating a heatmap that facilitates predicting prostate cancer. In one embodiment, the digitized image data comprises a set of pixels and gray-level data about the set of pixels. In one embodiment, detecting CaP in a MR image of a prostate of a CaP patient comprises learning a weighted vector based in part on MsLBP of positive cancerous and negative non-cancerous tissue in the image, selecting a template LBP from the image, performing an exhaustive weighted Hamming matching of the image on a pixel-by-pixel basis, and generating a heatmap based, at least in part, on the weighted vector and the exhaustive search. In different examples, the set of logics 630 may be permanently and/or removably attached to computer 600.

Processor 602 can be a variety of various processors including dual microprocessor and other multi-processor architectures. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a flash memory card, or a memory stick. Furthermore, disk 606 may include optical drives like a CD-ROM or a digital video ROM drive (DVD ROM). Memory 604 can store processes 614 or data 616, for example. Disk 606 and/or memory 604 can store an operating system that controls and allocates resources of computer 600.

Bus 608 can be a single internal bus interconnect architecture or other bus or mesh architectures. While a single bus is illustrated, it is to be appreciated that computer 600 may communicate with various devices, logics, and peripherals using other busses that are not illustrated (e.g., PCIE, SATA, Infiniband, 1394, USB, Ethernet).

Computer 600 may interact with input/output devices via I/O interfaces 618 and input/output ports 610. Input/output devices can include, but are not limited to, MRI scanners configured to acquire T2-weighted MRI images, a keyboard, a microscope, a microphone, a pointing and selection device, cameras, video cards, displays, disk 606, network devices 620, and other devices. Input/output ports 610 can include but are not limited to, serial ports, parallel ports, and USB ports.

Computer 600 may operate in a network environment and thus may be connected to network devices 620 via I/O interfaces 618, or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), and other networks.

In one example, a method may be implemented as computer executable instructions. Thus, in one example, a computer-readable storage medium may store computer executable instructions that if executed by a machine (e.g., computer) cause the machine to perform methods described or claimed herein including method 100 and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer cause the computer to perform a method associated with detecting prostate cancer (CaP) in a magnetic resonance (MR) image of a prostate of a CaP patient, the method comprising:
   accessing a digitized MR image of the prostate, where the digitized MR image comprises a set of pixels and gray-level intensity information about the pixels;
   labelling one or more pixels in the digitized MR image as positive pixels;
   labelling one or more pixels in the digitized MR image as negative pixels;
   extracting a local binary pattern (LBP) for a first pixel in the one or more positive pixels at a plurality of scales;
   extracting an LBP of a second pixel in the one or more negative pixels at the plurality of scales;
   calculating a first Hamming distance for the one or more positive pixels and the one or more negative pixels at the plurality of scales;
   learning a vector, where the vector weighs the first Hamming distance at the plurality of scales;
   generating a template LBP by extracting an LBP from a template pixel in a non-empty subset of the set of pixels;
   calculating second Hamming distances of the template LBP and of the LBP of a pixel other than the template pixel in the set of pixels at the plurality of scales;
   calculating a weighted sum of the second Hamming distances at the plurality of scales as a function of the second Hamming distances and the vector;
   generating a statistical probability heatmap based, at least in part, on the weighted sum, where co-ordinates of the heatmap with higher probability indicate a higher probability that a region of the prostate corresponding to the co-ordinate is cancerous, and
   displaying the statistical probability heatmap to distinguish between cancerous and benign tissue on a per-pixel basis.

2. The non-transitory computer-readable storage medium of claim 1, where the digitized MR image is a T2 weighted magnetic resonance imaging (MRI) image.

3. The non-transitory computer-readable storage medium of claim 2, where an LBP comprises an LBP number, the LBP number comprising the signs of a gray-level intensity value discrepancy between a gray-level intensity value of a first pixel from the digitized MR image represented by $f_c$ and the gray-level intensity values of p equally spaced sampled pixels on a circle of radius $x=\sum_{i=0}^{p-1} \text{sign}(f_i - f_c) 2^i$ in the digitized MR image, where p is an integer, where $f_i$, $i \in \{0, 1, \ldots, p-1\}$ is the gray-level intensity value of an i-th sampled pixel, and where sign is a sign function defined as $$\text{sign}(y) = \begin{cases} 1, & \text{if } y \geq 0; \\ 0, & \text{if } y < 0. \end{cases}$$

4. The non-transitory computer-readable storage medium of claim 3, where co-ordinates of $f_i$ are given by $$\left( -r \sin\left(\frac{2\pi i}{p}\right), r \cos\left(\frac{2\pi i}{p}\right) \right),$$

where the co-ordinates of $f_i$ within the circle together form a circularly symmetric neighbor set, where r is the radius of the circle, where r is fixed as $r \in \{4, 8, 12, 14, 16, 20, 24, 28, 32, 36\}$, and where $p \in \{8, 16, 32, 64\}$.

5. The non-transitory computer-readable storage medium of claim 4, where a binomial factor $2^i$ transforms the LBP to a number, where the bits of the number are measured in Hamming distance, where the LBP is invariant to local gray-scale shift, and where a circular bitwise right shift is performed p times on p bits within the circle, where the minimum resulting number of the circular bitwise right shift is retained as the final LBP.

6. The non-transitory computer-readable storage medium of claim 5, the method comprising finding a similarity between a pair of LBPs at the plurality of scales, where the similarity is computed as a dissimilarity metric, where the dissimilarity metric is measured by a kernel defined as $H(x, x') = \sum_{n=1}^{N} d_H(x_n, x_n')$, where N is a number of operations of varying (p, r), where $d_H(x_n, x_n')$ is the Hamming distance, where $d_H = \sum_{i=0}^{p-1}(x_i \neq x_i')$, where $x_i$ is the i-th bit of x, and $x_i'$ is the i-th bit of x'.

7. The non-transitory computer-readable storage medium of claim 6, where the dissimilarity metric is a weighted sum defined as $H(x, x') = \sum_{n=1}^{N} w_n d_H(x_n, x_n') = w^T b_H$, where $w \in [0, 1]$ is a weight for a scale in the plurality of scales, where $w \in R^{N \times 1}$, and where $b_H$ is a column vector of $d_H(x_n, x_n')$.

8. The non-transitory computer-readable storage medium of claim 7, where learning a vector comprises calculating a minimized objective function $\min_w \sum_{x \in P, x' \in P} H^2(x, x') - \alpha \sum_{x \in P, x' \in N} H^2(x, x')$, such that $1 \geq w_n \geq 0$, $n=1, \ldots, N$, and $\sum_{n=1}^{N} w_n = 1$, where P is a set of the one or more positive pixels in the digitized MR image classified as positive, where N is a set of the one or more negative pixels in the digitized MR image classified as negative, where $\alpha$ balances an intra-class Hamming distance and an inter-class Hamming distance, and where $1 \geq w_n \geq 0$ constrains that $w_n$ is a weight and that $w_n$ satisfies $\sum_{n=1}^{N} w_n = 1$.

9. The non-transitory computer-readable storage medium of claim 8, where combining the minimized objective function with the weighted sum results in $\sum_{x \in P, x' \in P} w^T b_H b_H^T w - \alpha \sum_{x \in P, x' \in PN} w^T b_H b_H^T w = w^T \Sigma_P w - \alpha w^T \Sigma_{PN} w$, where $\Sigma_P = \sum_{x \in P, x' \in P} b_H b_H^T$ is the intra-class Hamming distance, and where $\Sigma_{PN} = \sum_{x \in P, x' \in N} b_H b_H^T$ is the inter-class Hamming distance.

10. The non-transitory computer-readable storage medium of claim 9, where the minimized objective function is expressed in matrix form as $\min_w w^T (\Sigma_P - \alpha \Sigma_{PN}) w$ such that $b^T w=1$ and $0 \leq w \leq 1$, where $b=[1, \ldots, 1]^T$, $b \in R^{N \times 1}$, where $\Sigma_P - \alpha \Sigma_{PN}$ is symmetric, and where $\alpha$ is chosen to keep $\Sigma_P - \alpha \Sigma_{PN}$ positive definite.

11. The non-transitory computer-readable storage medium of claim 10, where the minimized objective function is solved using interior-point optimization.

12. The non-transitory computer-readable storage medium of claim 11, where generating a statistical probability heatmap comprises selecting a query pixel from the image, calculating the weighted sum $H(x, x') = \Sigma_{n=1}^{N} w_n d_H(x_n, x_n') = w^T b_H$ based, at least in part, on the query pixel, and indexing the image based on the weighted sum and the query pixel.

13. A non-transitory computer-readable storage medium storing computer executable instructions that when executed by a computer cause the computer to perform a method, the method comprising:
    accessing an input image, where the input image is a digitized image comprising a set of pixels and intensity information about the set of pixels;
    labelling a non-empty subset of pixels in the input image as a positive set;
    labelling a non-empty subset of pixels in the input image as a negative set, where the negative set does not include the positive set;
    computing a first sum of positive local binary pattern (LBP) descriptors as a function of the positive set;
    computing a second sum of negative and positive LBP descriptors as a function of the negative set and the positive set;
    computing a weighted vector from the first sum of positive LBP descriptors and the second sum of negative and positive LBP descriptors;
    extracting a multiscale LBP at a co-ordinate from the input image at a plurality of scales;
    finding the Hamming distance of the multiscale LBP at the plurality of scales;
    computing a weighted sum as a function of the transpose of the weighted vector and a column vector of the Hamming distance of the multiscale LBP;
    assigning the weighted sum for the co-ordinate to a statistical probability heatmap of the input image;
    updating a memory to store the statistical probability heatmap, and
    controlling a display to display the statistical probability heatmap, where the statistical probability heatmap facilitates distinguishing regions of the input image associated with the positive set and regions of the input image associated with the negative set.

14. The non-transitory computer-readable storage medium of claim 13, where computing a weighted vector w comprises optimizing $\min_w w^T (\Sigma_P - \alpha \Sigma_{PN}) w$ such that $b^T w=1$ and $0 \leq w \leq 1$, where $b=[1, \ldots, 1]^T$, $b \in R^{N \times 1}$, where P is the first sum, where PN is the second sum, where $\Sigma_P - \alpha \Sigma_{PN}$ is a symmetric matrix, where $\alpha$ is chosen to keep $\Sigma_P - \alpha \Sigma_{PN}$ positive definite, and where N is a number of operations of varying (p, r), where p is a set of equally spaced pixels on a circle with radius r of the input image.

15. The non-transitory computer-readable storage medium of claim 14, where computing the weighted sum comprises computing $w^T b_H = \Sigma_{n=1}^{N} w_n d_H(x_n, x_n') = H(x, x')$, where $d_H(x_n, x_n')$ is the Hamming distance, where $d_H = \Sigma_{i=0}^{p_r-1} (x_i \neq x_i')$, where $x_i$ is the i-th bit of x, and $x_i'$ is the i-th bit of x'.

16. An apparatus comprising:
    a processor;
    a memory;
    an input/output interface;
    a set of logics; and
    an interface to connect the processor, the memory, the input/output interface and the set of logics, the set of logics comprising:
        an image acquisition logic that acquires an image of a region of tissue;
        a learning logic that learns a weighted vector based, at least in part, on the image;
        a salient feature detection logic that detects salient features in the image, based, at least in part, on the weighted vector, and
        a prediction logic that generates a heatmap that distinguishes salient features from non-salient features in the image.

17. The apparatus of claim 16, where the learning logic extracts a set of positive salient feature sample pixels from a magnetic resonance (MR) image of a region of tissue, extracts a set of negative non-salient feature pixels from the image, extracts multiscale local binary pattern (MsLBP) codes from the set of positive sample pixels and the set of negative sample pixels, and computes a weighted vector by discriminatively training a vector that weighs the Hamming value of a pixel at a plurality of scales.

18. The apparatus of claim 17 where the salient feature detection logic iteratively selects a template pixel from the image, searches over the image to match the local binary pattern (LBP) of a pixel in the image with the LBP of the template pixel at a plurality of scales, finds the Hamming distance for the pixel at a plurality of scales, and computes a weighted sum as a function of the weighted vector and a column vector of the Hamming distance.

19. The apparatus of claim 18, where the prediction logic generates a statistical probability heatmap based, at least in part on the weighted sum, where hotter regions of the heatmap have a higher probability of indicating a salient feature, and where cooler regions of the heatmap have a lower probability of indicating a salient feature.

20. An apparatus comprising:
    a processor;
    a memory;
    an input/output interface;
    a set of logics; and
    an interface to connect the processor, the memory, the input/output interface and the set of logics, the set of logics comprising:
        a first logic that generates a weighted vector;
        a second logic that determines a similarity between a template pixel and another pixel in an image based, at least in part on the weighted vector; and
        a third logic that facilitates predicting cancer by producing a heatmap of the image based, at least in part, on the weighted vector and the similarity.

* * * * *